United States Patent [19]

Sanders et al.

[11] Patent Number: 4,764,379
[45] Date of Patent: Aug. 16, 1988

[54] TRANSDERMAL DRUG DELIVERY DEVICE WITH DUAL PERMEATION ENHANCERS

[75] Inventors: Harold F. Sanders, San Jose; Yu-Ling Cheng, Cupertino; David J. Enscore, Sunnyvale; Shari B. Libicki, Palo Alto, all of Calif.

[73] Assignee: Alza Corporation, Palo Alto, Calif.

[21] Appl. No.: 88,767

[22] Filed: Aug. 24, 1987

[51] Int. Cl.$^4$ .............................................. A61F 13/00
[52] U.S. Cl. .................... 424/449; 424/448; 514/946; 514/943
[58] Field of Search ............... 424/448, 449; 514/946, 514/947

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,031,894 | 6/1977 | Urquhart et al. | 128/268 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,568,343 | 2/1986 | Leeper et al. | 604/896 |

FOREIGN PATENT DOCUMENTS 10001949 8/1985 Fed. Rep. of Germany .

OTHER PUBLICATIONS

Idson B., "Percutaneous Absorption", Journal of Pharmaceutical Sciences, vol. 64, No. 6 (Jun. 1975), pp. 901-924.

Primary Examiner—Thurman K. Page
Assistant Examiner—J. R. Horne
Attorney, Agent, or Firm—Shelley G. Precivale; Edward L. Mandell; Steven F. Stone

[57] ABSTRACT

A dosage form that coadministers a drug and two percutaneous adsorption enhancers to a defined area of the skin is described. The dosage form comprises a body that contains supplies of drug and enhancers and has a basal surface that contacts the area of skin and transmits the drug and enhancers to the area for absorption thereby.

25 Claims, 3 Drawing Sheets

TRANSDERMAL DRUG DELIVERY DEVICE WITH DUAL PERMEATION ENHANCERS

FIELD OF THE INVENTION

This invention relates to systems for drug delivery. More particularly, this invention relates to transdermal drug delivery and still more particularly, but without limitation thereto, this invention relates to the transdermal delivery of drugs utilizing a combination of two permeation enhancers.

RELATED PATENT APPLICATIONS

This invention is related to the invention disclosed in the copending, coassigned patent application Ser. No. 07/019,470 of Cheng et al, for Skin Permeation Enhancer Compositions Using Glycerol Monolaurate, filed Feb. 26, 1987.

BACKGROUND OF THE INVENTION

The transdermal route of parenteral delivery of drugs provides many advantages over other administrative routes and transdermal systems for delivering a wide variety of drugs or other beneficial agents are described in U.S. Pat. Nos. 3,598,122; 3,598,123; 4,379,454; 4,286,592; 4,314,557 and 4,568,343, for example, all of which are incorporated herein by reference.

However, despite the development of the art, there has remained a continuing need for improved techniques in drug delivery and improved drug delivery systems.

The present invention delivers drugs at therapeutically effective rates and offers the advantages of greatly increased drug permeability through the skin, along with reduction of the lag time between application of a transdermal therapeutic system and attainment of the desired drug flux.

While it is known in the art to combine permeation enhancers, this invention utilizes a novel combination of ethanol and glycerol monolaurate (GML) and the combined effect is a signficant and surprising improvement over use of ethanol or glycerol monolaurate, alone.

SUMMARY OF THE INVENTION

An object of the present invention is to provide drug delivery by means of transdermal systems.

A further object is to increase the transport of drugs across the skin following application of a transdermal therapeutic system.

A still further object of the present invention is to deliver drugs transdermally using a combination of two permeation enhancers.

Another object of this invention is to eliminate the lag time between application of a transdermal therapeutic system and attainment of the desired therapeutic flux level.

An even further object is to provide a method for the transdermal administration of calcium channel blockers, specifically nilvadipine.

These and other objects have been demonstrated by the present invention wherein a transdermal system is designed to deliver a drug and both glycerol monolaurate and ethanol to enhance skin permeability.

BRIEF DESCRIPTION OF THE DRAWING

The invention will be described in further detail with reference to the accompanying drawings wherein.

DESCRIPTION OF THE PREFERRED EMBODIMENT

This invention utilizes principles of transdermal drug delivery to provide a novel system for effectively administering drugs. Of particular significance is the use of codelivered permeation enhancers, specifically to aid in delivery of drugs across the skin. While both ethanol and glycerol monolaurate are known permeation enhancers, their combined effect provides a surprising increase in the flux of drug across the skin, as is illustrated in FIG. 1.

Figure 1:
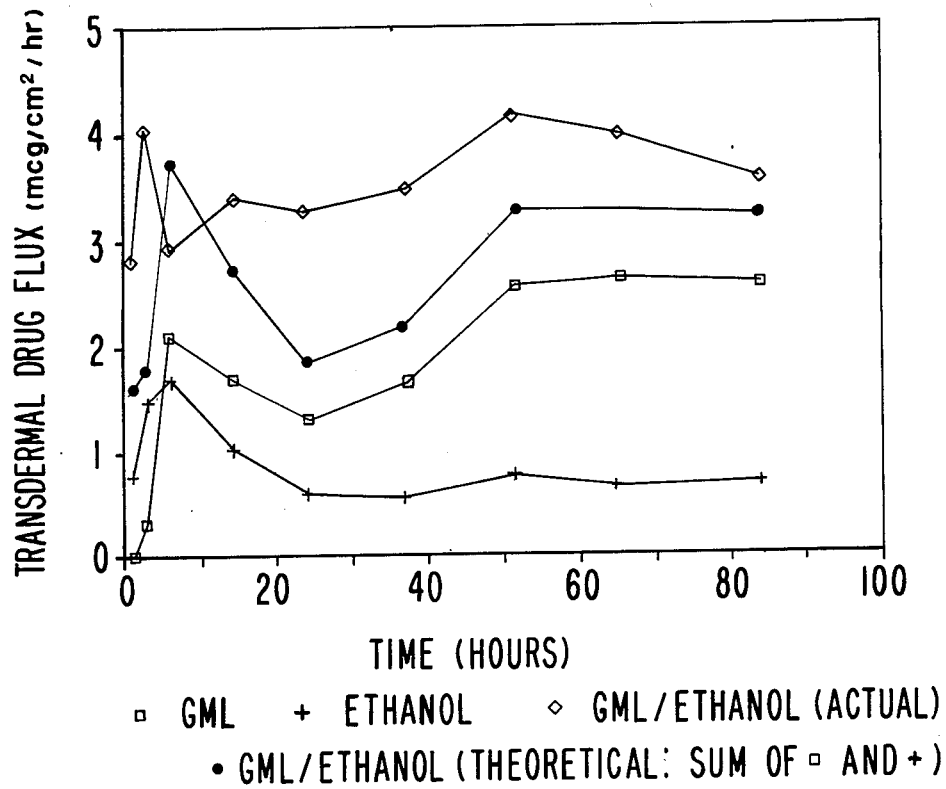
FIG. 1 is a graph of transdermal drug flux (across cadaver skin, 35° C.) of nilvadipine versus time for glycerol monolaurate and ethanol, both alone and in combination.

FIG. 1 charts the actual drug flux (cadaver skin, 35° C.) attained using ethanol alone, glycerol monolaurate alone, and ethanol and glycerol monolaurate in combination. Additionally, a theoretical plot is presented of the flux that such a combination would be expected to provide. As is seen by FIG. 1, the actual flux attained with the combined permeation enhancers is significantly greater than the sum of the drug fluxes obtained with the individual enhancers (i.e., the theoretical flux).

In general, the scope of the invention encompasses a composition of matter comprising a drug and two permeation enhancers: ethanol and glycerol monolaurate.

Specifically, the invention can be a unit dosage form and method that coadministers a drug and a combination of two percutaneous absorption enhancers to a predetermined area of the skin.

In a preferred embodiment, an excess of drug is administered to the skin and at least one of the percutaneous absorption enhancers is coadministered at a controlled, preferably substantially constant rate. The coadministered permeation enhancers increase the permeability of the treated area of the skin to the drug such that the rate of drug administration is determined by the rate at which the treated skin absorbs the drug.

More specifically, the dosage form comprises a body:
(a) having a basal surface
  (i) of area at least about equal to the area of skin to be treated,
  (ii) that is adapted to contact the area of skin over the time period, and
  (iii) via which the drug and enhancers are presented to the area of skin for the absorption thereby;
(b) containing a supply of the drug that communicates with the basal surface to provide drug at the basal surface over the time period;

(c) containing supplies of both percutaneous absorption enhancers which communicate with the basal surface so as to provide the enhancers at the basal surface over said time period; and (d) optionally including means for maintaining the rate at which at least one of the enhancers is provided at the basal surface.

In one embodiment, the supply of drug is such that over a substantial portion of the time period, the amount of drug provided to the basal surface is in excess of that which the area of treated skin is able to absorb, and the rate at which one of the enhancers is provided is substantially constant over a substantial portion of the time period, the rate being (i) below the maximum rate the area of skin is able to absorb, and (ii) sufficient with the coadministration of the other enhancer to substantially increase the permeability of the area of skin to the drug.

Correlatively, the method of this invention comprises:

(a) administering the drug to the area over the time period; and (b) simultaneously coadministering two percutaneous absorption enhancers to the area of skin.

In a separate embodiment of the method of this invention, the drug is administered such that over a substantial portion of the time period the amount of drug administered is in excess of that which the area of treated skin is able to absorb and at least one enhancer is administered at a rate that is substantially constant over a substantial portion of the time period, the rate being (i) below the maximum rate the area of skin is able to absorb, and (ii) sufficient with the coadministration of the other enhancer to substantially increase the permeability of the area of skin to the drug.

As used herein the term "substantial portion of the time period" means at least about 60% of the time period, preferably at least about 90% of the time period. Correlatively, the term "substantially constant" means a variation of less than about ±20%, preferably less than about ±10%, over a substantial portion of the time period.

It is believed that this invention has utility in connection with the delivery of drugs within the broad class normally delivered through body surfaces and membranes, including skin. Specifically, it is anticipated that this invention will be useful in the delivery of drugs whose permeability can be enhanced by ethanol and glycerol monolaurate, such as estradiol and its esters, ergonovine and ergot alkaloids, and opiates and narcotic analgesics such as naltrexone, nalbuphine, naloxone, hydromorphone, levorphanol, morphine and its analogs.

As used herein, the expressions "drug" and "agent" are used interchangeably and are intended to have their broadest interpretation as to any therapeutically active substance which is delivered to a living organism to produce a desired, usually beneficial, effect. In general, this includes therapeutic agents in all of the major therapeutic areas, including, but not limited to, anti-infectives such as antibiotics and antiviral agents, analgesics and analgesic combinations, anorexics, antiarthritics, antiasthmatic agents, anticonvulsants, antidepressants, antidiabetic agents, antidiarrheals, antihistamines, antiinflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, psychostimulants, sedatives and tranquilizers.

The above described composition of matter, dosage form and method are especially useful for coadministering nilvadipine, ethanol and glycerol monolaurate percutaneously. Nilvadipine is a calcium channel blocker and is used to treat conditions associated with heart disease. This invention is particularly suited for the transdermal administration of nilvadipine and its stereo isomers as chronic therapy for hypertension.

Figure 2:
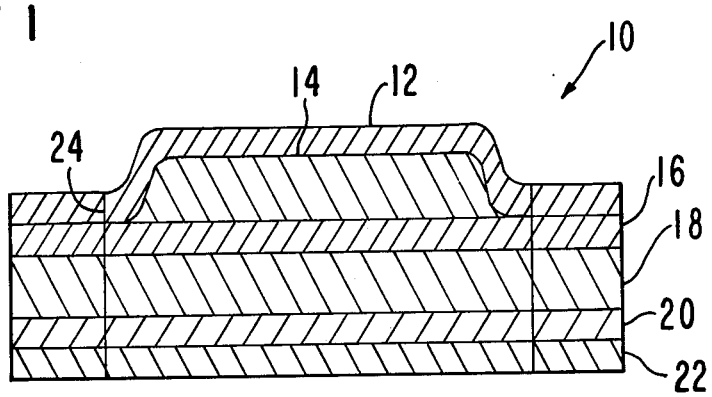
FIG. 2 is a cross-sectional view of one embodiment of the transdermal drug delivery system according to this invention, utilizing a rate controlling membrane.

One embodiment of the invention is best understood with reference to FIG. 2, which illustrates a transdermal drug delivery system 10. System 10 is a multilaminate system comprised of five layers: a top impermeable backing layer 12, an ethanol gel layer 14, and a rate controlling membrane 16, a drug reservoir 18, an adhesive layer 20 and a strippable release liner 22. The drug reservoir 18 is comprised of a polymeric matrix or carrier having the drug to be delivered, dispersed throughout.

The system 10 is held in place by means of an in-line pharmaceutically acceptable contact adhesive 20. Drug and/or glycerol monolaurate may also be incorporated into the adhesive layer 20. The composition and thickness of the adhesive layer are such that it does not constitute a significant permeation barrier to the drug or the enhancers. During the time interval between the manufacture and use of the system 10, adhesive layer 20 may absorb enhancers and drug in amounts that will depend upon the composition and thickness of layer 20 and the length of that time interval. If that interval is quite long, layer 20 will absorb both drug and enhancers until it is saturated with said components. The release of such absorbed enhancers from layer 20 once the system is applied to the skin may cause the release rate of the enhancers to exceed the desired steady-state rate for a short period of time. The condition will be transient and will not affect the functionality of the system in providing controlled therapy. Contact adhesive compositions that are suitable for use as layer 20 are disclosed in U.S. Pat. Nos. 3,797,494 and 4,031,894.

A strippable release liner 22, adapted to be removed prior to application, would normally be included in the packaged product.

The permeation enhancer, glycerol monolaurate, may be contained either within the ethanol gel layer 14 or the drug reservoir 18, or both. Particularly suitable for use in this invention is a brand of glycerol monolaurate sold under the name Grindtek ML 90 (Grindsted Products, Industrial Airport, Kansas).

Layer 14 is a continuous ethanol phase, which may also contain one or more covehicles, such as water. Preferably the continuous phase is in the form of a gel that contains 5% to 75% by weight water. Known gelling agents such as carboxypolymethylene, ethylene maleic anhydride, hydroxyethylcellulose, polyacrylamide, ethylhydroxyethylcellulose, hydroxypropylcellulose, and poly(methylvinylether-maleic anhydride)

may also be included in the continuous phase to make it gel. Layer 14 may also include diluents, stabilizers, vehicles, gelling agents, and the like.

The rate controlling membrane 16 may be fabricated from permeable, semipermeable or microporous materials which are known in the art to control the rate of agents into and out of delivery devices. Suitable materials include polyvinylacetate and ethylene vinylacetate polymers.

The size of the system of this invention can vary from less than 1 cm² to greater than 200 cm². The average system however, will have a size within the range of about 5–50 cm².

Various materials suited for the fabrication of the various layers are disclosed in the aforementioned patents. The polymer matrix of the drug reservoir 18 is preferably anhydrous and suitable materials include, without limitation, natural and synthetic rubbers or other polymeric material, thickened mineral oil, or petroleum jelly. The preferred embodiment according to this invention is fabricated from an ethylene/vinylacetate (EVA) copolymer of the type described in U.S. Pat. No. 4,144,317, preferably those having a vinylacetate content in the range of about 28 to 60 weight percent. Particularly good results have been obtained using an EVA copolymer of 40 weight percent vinylacetate content (EVA 40).

The drug reservoir 18 may contain the drug alone or it may contain the drug along with the permeation enhancer, glycerol monolaurate. The amount of drug in the reservoir will depend upon the rate at which the drug is absorbed by the skin from the system and the intended duration of therapy. The reservoir 18 may also include diluents, stabilizers, vehicles, gelling agents, and the like.

Certain drugs are highly soluble in ethanol. In those cases, the ethanol gel layer is initially saturated with drug to insure that the drug contained within matrix 18 will diffuse towards the skin rather than into the ethanol gel. Nilvadipine is one such drug. Therefore, a system such as that in FIG. 2 would have a saturation concentration of nilvadipine in the ethanol gel layer 14 and the amount of drug which is ultimately to be delivered will be contained within the polymeric matrix (reservoir) 18.

Embodiments such as system 10 in which the drug and enhancer supplies are separate may be advantageous or necessary in instances where formulation or storage of the drug and enhancers in contact with each other is impractical or undesirable or where separation of the drug and enhancers facilitate selection of the rate controlling membrane.

System 10, as stated above, may optionally contain glycerol monolaurate in the ethanol layer 14, in the drug reservoir 18 and in the adhesive 20. The critical constraint is that glycerol monolaurate must be present for the system to deliver drug at the therapeutically desired rate. Regardless of where glycerol monolaurate is placed during manufacturing, it will eventually equilibriate into the other layers.

The amount of ethanol and glycerol monolaurate in the system will depend upon the rates at which the enhancers need to be administered to the skin from the system to achieve the desired degree of drug permeability enhancement over the treatment period. However, glycerol monolaurate is highly soluble in ethanol and if admixed in the same reservoir, glycerol monolaurate would be present in below saturation concentration.

The backing member 12 serves the purpose of both preventing passage of the drug and permeation enhancers through the surface of the gel layer distant from the skin, and also of providing support for the system, where needed. The backing layer can be flexible or nonflexible and suitable materials include, without limitation, cellophane, cellulose acetate, ethylcellulose, plasticized vinylacetate-vinylchloride copolymers, polyethylene terephthalate, nylon, high and low density polyethylene, polypropylene, metalized polyester films, polyvinylidene chloride, coated flexible fibrous backings such as paper and cloth and aluminum foil. Such backings can be in the form of precast films or fabrics which are bonded to the reservoir by heat or adhesives and can be coated onto the reservoir. The preferred embodiment utilizes a heat sealable backing membrane, such that the system is sealed around its periphery. This helps to prevent any evaporation of the ethanol. The heat seal is shown in FIG. 2, by line 24.

In operation, system 10 is applied to a relatively non-hairy area of the skin that is preferably substantially free of wrinkles, creases or folds. Various locations on the torso, such as the flank or shoulder, provide suitable sites for the transdermal system. Once the system is placed on the skin, it will begin coadministering drug, ethanol and glycerol monolaurate, to the wearer.

Figure 3:
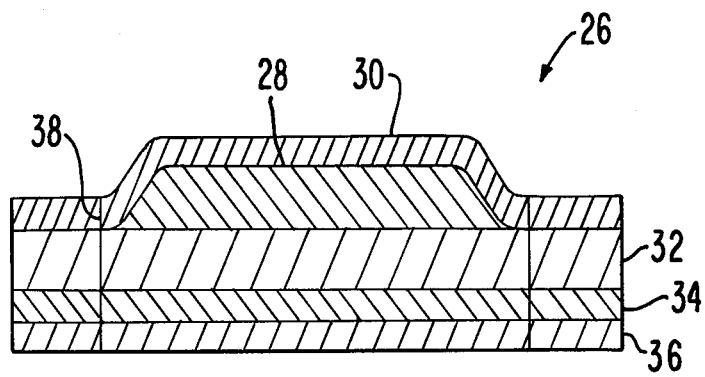
FIG. 3 is a cross-sectional view of another embodiment of the transdermal drug delivery system of this invention.

A second embodiment of the invention is shown in FIG. 3. The transdermal drug delivery system 26 comprises an ethanol gel layer 28, backing member 30, drug polymer matrix 32, adhesive layer 34 and strippable release liner 36. As with the embodiment of FIG. 2, the ethanol layer 28 and/or the drug polymeric matrix 32 may have a specified amount of glycerol monolaurate incorporated therein. Additionally, glycerol monolaurate may be incorporated into the adhesive 34. In this embodiment of the invention, the rate controlling membrane has been omitted. As with system 10, system 26 is preferably heat sealed around its periphery, as indicated by line 38.

Figure 4:
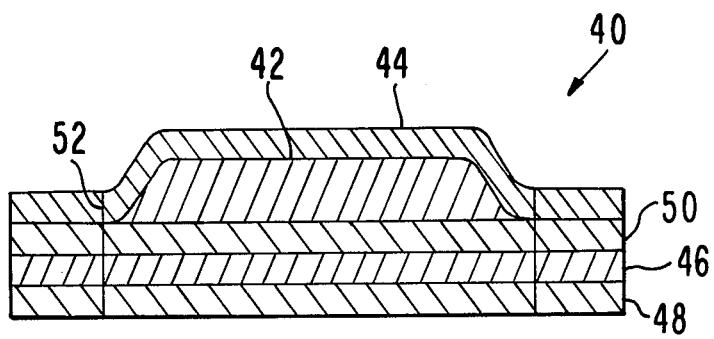
FIG. 4 is a cross-sectional view of still another embodiment of the transdermal drug delivery system according to this invention, utilizing a rate controlling membrane.

Another embodiment of the invention is shown in FIG. 4. System 40 incorporates the drug into the ethanol gel layer 42 rather than in a separate reservoir. The ethanol gel/drug layer 42 also contains a specified amount of the permeation enhancer glycerol monolaurate. The system has an impermeable backing 44 and a pharmaceutically acceptable in-line contact adhesive 46 which may contain a specified amount of drug and/or glycerol monolaurate. System 40 also has a strippable release liner 48. System 40 is further provided with a rate controlling membrane 50. The entire system is the sealed along its periphery, as shown by line 52.

The drug is present either wholly in solution or in both dissolved and undissolved form dispersed uniformly through a continuous ethanol phase. The continuous phase contains drug over the lifetime of the system and the minimum amount of drug in layer 42 will depend on its solubility in the continuous phase and the intended lifetime of system 40. Layer 42 may include diluents, stabilizers, vehicles, gelling agents and the like, in addition to the drug and enhancers. This layer may also contain one or more covehicles, such as water, to alter the solubility of the drug in said phase.

The amount of drug in layer 42 will depend on the rate at which the drug is absorbed by the skin from the system and the intended duration of therapy. Correlatively, the amount of enhancers in the reservoir will depend upon the rate at which the enhancers are administered to the skin from the system to achieve the desired degree of drug permeability enhancement over the treatment period.

Rate controlling membrane 50 may be made of a dense or microporous polymer film that has the requisite permeability to the drug and enhancers. This membrane controls the rate at which at least one of the enhancers is administered to the skin. It does not, however, control the rate at which the drug is administered. In other words, it is a principal permeation barrier to at least one of the enhancers, but not a significant permeation barrier to the drug. The respective fluxes of the drug and enhancers through layer 50 will depend upon the thickness of the layer and the permeabilities of the drug and the enhancers through the layer. Permeabilities may be determined by standard techniques. Accordingly, films that will permit the required fluxes of drug and enhancers may be selected based on permeabilities and thickness. Preferably the rate controlling membrane 50 is substantially impermeable to other components of layer 42. Examples of the types of polymer films that may be used to make layer 50 are disclosed in U.S. Pat. Nos. 3,797,494 and 4,031,894, both of which are incorporated herein by reference.

Figure 5:
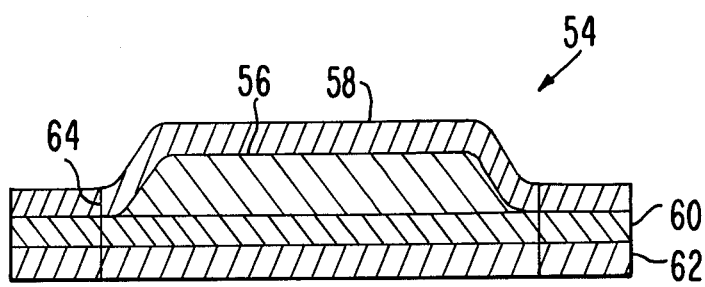
FIG. 5 is a cross-sectional view of yet another embodiment of the transdermal drug delivery system of this invention.

FIG. 5 illustrates still another embodiment of the invention, system 54, where the drug to be delivered is incorporated into the ethanol gel layer 56 which also contains glycerol monolaurate. As with system 40, system 54 is comprised of an impermeable backing 58, an in-line contact adhesive 60 which may also have drug and/or glycerol monolaurate incorporated therein, and a strippable release liner 62. System 54 is also heat sealed around its periphery, as illustrated by line 64. In this embodiment, the rate controlling membrane has been omitted.

Figure 6:
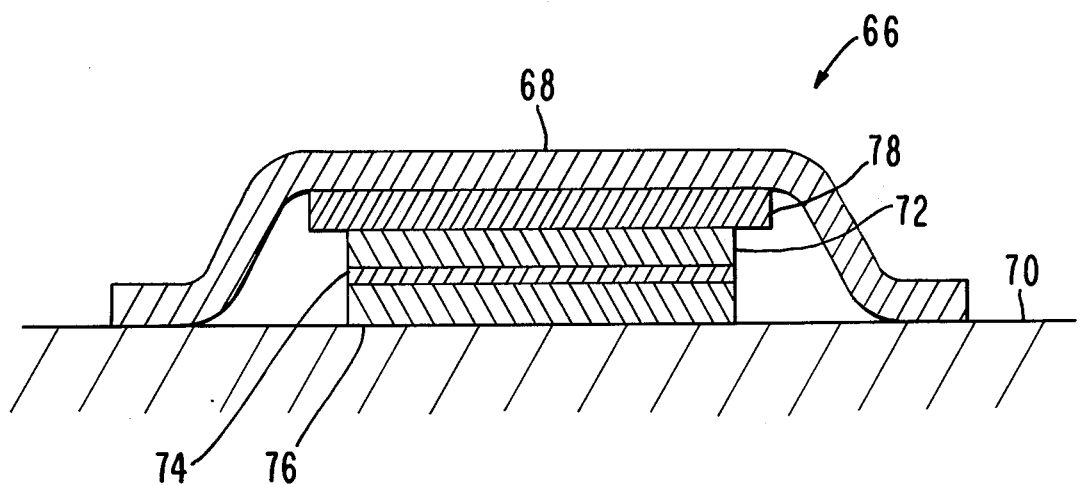
FIG. 6 is a cross-sectional view of another embodiment of the transdermal drug delivery system according to this invention, utilizing an adhesive overlay.

FIG. 6 illustrates a system 66 which provides for an adhesive overlay 68 to position the system on the skin 70. Means 68 for adhering the system to the skin may be fabricated together with or separately from the remaining elements. The multilaminate system 66 is comprised of an ethanol gel layer 72, a rate controlling membrane 74 and a drug reservoir 76.

In some instances, an adhesive overlay is preferable over an in-line contact adhesive. This is true when there are elements present in the system which may adversely affect the adhesive properties of the contact adhesive. For this reason, impermeable backing layer 78 is preferably sized slightly larger than the ethanol reservoir 72 to provide a peripheral area around the reservoir 72, which would be free of any material which may seep from under the base of reservoir 72 and adversely interact with the adhesive in overlay 68. A strippable release liner would also be provided with the system 66, to be removed prior to use.

Layers 72 and 76 are of the same composition as those described in relation to the embodiments of FIGS. 2 through 5. Additionally, the systems illustrated in FIGS. 2-5 can be readily adapted to an adhesive overlay configuration in lieu of the in-line contact adhesive.

EXAMPLE I

Three test samples were made to measure the drug flux (mcg/cm2/hr) attainable with ethanol (EtOH) alone, glycerol monolaurate (GML) alone, and the two enhancers (EtOH/GML) combined.

Sample I: drug and ethanol. A casting solution was mixed for the monolithic portion of the test sample (I) comprising 30 weight percent (w %) nilvadipine and 70 w % EVA 40 (40% vinylacetate content). Methylene chloride was used as a solvent. This mix was cast at a Gardner knife setting of 25 mils and dried. The monolith was then heat laminated to a 2 mil thick EVA (9% vinylacetate) rate controlling membrane. A 95% ethanol gel was made comprising 98 w % of 95% ethanol and 2 w % hydroxypropylcellulose, and sealed to the EVA 9 membrane.

Sample II: drug and glycerol monolaurate. Using methylene chloride as the solvent, the monolithic portion of the test sample (II) was solution cast and dried as for test sample I. The composition was 30 w % nilvadipine, 40 w % glycerol monolaurate and 30 w % EVA 40. This monolith was then heat laminated to a MEDPAR backing.

Sample III: drug, ethanol and glycerol monolaurate. A casting solution, using methylene chloride solvent, was mixed for the monolithic portion of the test sample (III) comprising 30 w % nilvadipine, 30 w % glycerol monolaurate (Grindtek ML 90) and 40 w % EVA 40. This was cast and dried as for test sample I. The monolith was then heat laminated to a 2 mil thick EVA (9% vinylacetate) rate controlling membrane. A 95% ethanol gel was made as for test sample I, and was sealed to the EVA 9 membrane.

The transdermal drug fluxes (mcg/cm$^2$/hr) attainable with test samples I, II and III were compared using two specimens (A and B) of cadaver skin at 35° C. to provide the following data:

TABLE I

| | Transdermal Drug Flux, mcg/cm2/hr | | | | | |
|---|---|---|---|---|---|---|
| | Sample I EtOH | | Sample II GML | | Sample III EtOH/GML | |
| Time, hrs | A | B | A | B | A | B |
| 2.00 | 0.738 | 0.948 | 0.000 | 0.000 | 5.862 | 2.064 |
| 4.00 | 1.734 | 1.704 | 0.990 | 0.000 | 8.790 | 2.766 |
| 8.00 | 2.034 | 2.052 | 2.985 | 1.163 | 4.359 | 2.700 |
| 21.00 | 1.231 | 1.029 | 1.276 | 0.898 | 5.263 | 2.452 |
| 27.25 | 0.739 | 0.407 | 1.354 | 0.542 | 4.539 | 2.344 |
| 47.00 | 0.673 | 0.328 | 1.206 | 0.536 | 5.449 | 2.392 |
| 56.00 | 1.040 | 0.527 | 2.613 | 1.273 | 5.993 | 3.061 |
| 74.75 | 0.925 | 0.308 | 2.994 | 3.902 | 5.590 | 3.066 |
| 93.00 | 1.055 | 0.496 | 2.778 | 1.912 | 4.398 | 3.075 |

This data is presented graphically in FIG. 1. A curve plotting the sum of the flux values for Samples I and II, illustrate the cumulative effects of the individual enhancers. As can be seen, the combination of permeation enhancers according to this invention produce fluxes substantially greater than the sum of the individual enhancer values.

EXAMPLE II

A transdermal therapeutic system as described with respect to FIG. 2 for the delivery of nilvadipine would have the following composition: a MEDPAR backing layer 12; an ethanol gel reservoir 14 comprised mainly of a 95% ethanol gel (98 w % of 95% ethanol and 2 w % of hydroxypropylcellulose); an EVA 9 rate controlling membrane 16; a polymeric drug matrix 18 comprised of 30 w % nilvadipine, 30 w % glycerol monolaurate and 40 w % EVA 40; a pharmaceutically acceptable in-line contact adhesive 20 and a strippable release liner 22. The multilaminate system, being assembled, is then heat sealed. Because nilvadipine is extremely soluble in ethanol, the gel reservoir 14 will also contain a saturation concentration of the drug to insure that upon placement of the system on the skin, the drug will migrate into the skin rather than into the ethanol reservoir. Additionally, because the system is a closed one, during storage all of the components will achieve a state of equilibrium so that there will be ethanol present in the drug matrix and likewise glycerol monolaurate will be present in the ethanol reservoir.

EXAMPLE III

A transdermal therapeutic system as described with respect to FIG. 3 for the delivery of nilvadipine or any other suitable drug would have the same composition as that in Example II with the omission of the rate controlling membrane.: a MEDPAR backing layer 30; an ethanol gel reservoir 28 comprised mainly of a 95% ethanol gel (98 w % of 95% ethanol and 2 w % of hydroxypropylcellulose); a polymeric drug matrix 32 comprised of 30 w % nilvadipine or other suitable therapeutic agent, 30 w % glycerol monolaurate and 40 w % EVA 40; a pharmaceutically acceptable in-line contact adhesive 34 and a strippable release liner 36. The multilaminate system, being assembled, is then heat sealed. If the drug to be delivered is soluble in ethanol, the gel reservoir 28 will also contain a saturation concentration of the drug to insure that upon placement of the system on the skin, the drug will migrate into the skin rather than into the ethanol reservoir. Additionally, because the system is a closed one, during storage all of the components will achieve a state of equilibrium so that there will be ethanol present in the drug matrix and likewise glycerol monolaurate will be present in the ethanol reservoir.

EXAMPLE IV

A transdermal therapeutic system as described with respect to FIG. 4 for the delivery of a therapeutic agent would have the following composition: a MEDPAR backing layer 44; an enhancer/drug reservoir 42 which would be comprised mainly of 95% ethanol, glycerol monolaurate and the drug to be delivered; and EVA 9 rate controlling membrane 50; a pharmaceutically acceptable in-line contact adhesive 46 and a strippable release line 48.

This invention has been described in detail with particular reference to certain preferred embodiments thereof, but it will be understood that variations and modifications can be effected within the spirit and scope of the invention.

What is claimed is:

1. A unit dosage form for transdermally coadministering a drug, ethanol and glycerol monolaurate, to a predetermined area of unbroken skin of a patient for a predetermined time period, the dosage form comprising a body:
    having a basal surface of area at least about equal to the area of skin, that is adapted to contact the area of skin over said time period, and via which the drug, and the permeation enhancers ethanol and glycerol monolaurate, are presented to the area of skin for absorption thereby;
    containing a supply of the drug that communicates with the basal surface to provide drug at the basal surface over said time period;
    containing a supply of ethanol that communicates with the basal surface over said time period; and
    containing a supply of glycerol monolaurate that communicates with the basal surface over said time period.

2. The unit dosage form of claim 1. wherein said supply of drug provides drug such that over a substantial portion of said time period, the amount of drug provided is in excess of that which the area of the skin is able to absorb.

3. The unit dosage form of claim 1. which further comprises:
    a means for maintaining the rate at which at least one permeation enhancer is provided at the basal surface substantially constant over a substantial portion of the time period.

4. The unit dosage form of claim 3. wherein said means maintains the rate at which at least one enhancer is provided to the basal surface such that said rate is below the maximum rate the skin is able to absorb, and sufficient in combination with the other permeation enhancer to substantially increase the permeability of the area of skin to the drug.

5. The means of claim 4 wherein said means maintains the rate at which ethanol is provided to the basal surface.

6. The unit dosage of claim 1. wherein the basal surface is adhesive to the area of skin.

7. The unit dosage form of claim 1. wherein the supplies of drug, ethanol and glycerol monolaurate are admixed and contained within the same reservoir.

8. The unit dosage form of claim 1. wherein the supply of drug and the supplies of ethanol and glycerol monolaurate are maintained in separate reservoirs.

9. The unit dosage form of claim 3. wherein the means is a rate controlling membrane positioned between the supplies of ethanol and glycerol monolaurate and the basal surface through which the ethanol and glycerol monolaurate must permeate to reach the basal surface.

10. The unit dosage form of claim 3. wherein the rates at which ethanol and glycerol monolaurate are provided at the basal surface are above that rate at which the rate of absorption of the drug by the area of skin ceases to increase significantly as the rates at which the enhancers are provided, are increased.

11. A unit dosage form for coadministering a drug, and permeation enhancers ethanol and glycerol monolaurate, to a predetermined area of unbroken skin of a patient for a predetermined time period comprising a laminate body comprising:
    a backing lamina that is substantially impermeable to the passage of drug, ethanol and glycerol monolaurate, one face of which defines the uppermost exterior surface of said body;
    a reservoir lamina adjacent and below the opposite face that contains a supply of the drug, ethanol and glycerol monolaurate; and
    a contact adhesive lamina adjacent and below the reservoir lamina, one face of which defines a basal surface of the body that contacts and adheres to the area of skin over the time period, and through which the drug, ethanol and glycerol monolaurate permeate to the basal surface wherefrom they are absorbed by the area of skin.

12. The unit dosage form of claim 11. which further comprises a rate controlling membrane adjacent and below the reservoir lamina through which the drug, and enhancers ethanol and glycerol monolaurate permeate, wherein the composition and thickness of said membrane is such that at least one enhancer permeates therethrough at a substantially constant rate over a substantial portion of the time period, the substantially constant rate being below the maximum rate the area of skin is able to absorb and sufficient in combination with the other permeation enhancer to substantially increase the permeability of the area of skin to the drug.

13. The unit dosage form of claim 12. wherein ethanol permeates through said rate controlling membrane at a substantially constant rate.

14. A dosage form for administering nilvadipine percutaneously and continuously over a predetermined time period through a predetermined area of unbroken skin comprising a laminate body of:
   a backing layer that is substantially impermeable to nilvadipine, ethanol and glycerol monolaurate;
   a reservoir layer adjacent to the opposite face of the backing layer comprising nilvadipine and glycerol monolaurate dispersed in gelled ethanol; and
   a contact adhesive layer below the reservoir, one face of which is the basal surface of the body when the laminate body is affixed to the skin, the contact adhesive layer being permeable to nilvadipine, ethanol and glycerol monolaurate.

15. The dosage form of claim 14 wherein said laminate body further comprises a rate controlling membrane layer interposed between said reservoir and said adhesive layer, through which nilvadipine, ethanol and glycerol monolaurate are released continuously over said predetermined period from the reservoir after the body is affixed to the skin.

16. The dosage form of claim 14 wherein said laminate body further comprises a polymeric matrix layer having nilvadipine dispersed therethrough, positioned below said reservoir layer.

17. The dosage form of claim 16 wherein said laminate body further comprises a rate controlling membrane layer interposed between said reservoir and said polymeric matrix layer through which ethanol and glycerol monolaurate are released continuously over said predetermined period from the reservoir after the body is affixed to the skin.

18. The dosage form of claim 14 wherein the edges of the backing layer and the rate controlling membrane are sealed together so that the reservoir layer is wholly contained between the backing layer and the rate controlling membrane.

19. The dosage form of claim 17 wherein the edges of the backing layer and the rate controlling membrane are sealed together so that the reservoir layer is wholly contained between the backing layer and the rate controlling membrane.

20. A method for coadministering a drug, and permeation enhancers ethanol and glycerol monolaurate, to a predetermined area of unbroken skin of a patient for a predetermined time period comprising:
   administering the drug to the area continuously over the time period; and
   simultaneously coadministering ethanol and glycerol monolaurate to the area of the skin at rates which are sufficient to substantially increase the permeability of the area of the skin to the drug.

21. The method of claim 20 where said administering step provides drug such that over a substantial portion of the time period the amount of drug administered is in excess of that which the area of skin is able to absorb.

22. The method of claim 20 wherein said simultaneous coadministering step provides delivery of at least one enhancer at a rate which is substantially constant over a substantial portion of the time period, the rate being: below the maximum rate the area of the skin is able to absorb, and sufficient in combination with the other permeation enhancer to substantially increase the permeability of the area of the skin to the drug.

23. The method of claim 22 wherein ethanol is delivered at a substantially constant rate.

24. A method for providing nilvadipine delivery comprising:
   administering nilvadipine to a predetermined area of unbroken skin over a predetermined time period; and
   simultaneously coadministering permeation enhancers ethanol and glycerol monolaurate to the area of skin, where at least one permeation enhancer is provided at a substantially constant rate over a substantial portion of the time period.

25. The method of claim 24 wherein said ethanol is provided at a substantially constant rate.

* * * * *